United States Patent [19]
Hani et al.

[11] Patent Number: 5,424,435
[45] Date of Patent: Jun. 13, 1995

[54] 1-HYDROXY-6-SUBSTITUTED-2-PYRIDONES

[75] Inventors: Rahim Hani, Cheshire; Phillip T. Berkowitz, Woodbridge, both of Conn.

[73] Assignee: Olin Corporation, Cheshire, Conn.

[21] Appl. No.: 137,521

[22] Filed: Oct. 18, 1993

[51] Int. Cl.⁶ .................. C07D 211/84; C07D 211/88
[52] U.S. Cl. ............................. 546/296; 252/400.23
[58] Field of Search ................ 546/294, 296; 514/348

[56] References Cited
U.S. PATENT DOCUMENTS

| | | | |
|---|---|---|---|
| 3,883,545 | 5/1975 | Lohaus et al. | 546/294 |
| 4,185,106 | 1/1980 | Dittmar et al. | 424/263 |
| 4,401,770 | 8/1983 | Hance | 521/120 |
| 4,818,436 | 4/1989 | French et al. | 252/400.23 |
| 4,916,228 | 4/1990 | Reuschling et al. | 546/290 |
| 4,935,061 | 6/1990 | French et al. | 106/170 |

*Primary Examiner*—Alan L. Rotman
*Attorney, Agent, or Firm*—Dale L. Carlson

[57] ABSTRACT

The present invention relates to novel 1-hydroxy-6-substituted-pyridone compounds. Also disclosed is a process for producing the compound(s) and an antimicrobial composition comprising the compound(s) and at least one component selected from the group consisting of soaps, adhesives, coatings, elastomers, sealants, shampoos, skin care medicaments, cosmetics, paints and other polymer compositions.

18 Claims, No Drawings

1-HYDROXY-6-SUBSTITUTED-2-PYRIDONES

FIELD OF THE INVENTION

This invention relates to novel 1-hydroxy-6-substituted-2-pyridones, a process for their preparation, and their use as biocides. These compounds exhibit good biocidal activity, particularly antifungal activity.

BACKGROUND OF THE INVENTION

Compounds exhibiting biocidal activity are well known in the art. For example, pyrithione salts, such as zinc pyrithione, are known to provide excellent biocidal activity, including broad spectrum anti-bacterial and anti-fungal activity. There are many uses for these pyrithiones. By way of illustration, U.S. Pat. No. 4,818,436 discloses the use of pyrithiones in metal working fluids, U.S. Pat. No. 4,401,770 discloses urethane shoe inserts having antimicrobial activity; and U.S. Pat. No. 4,935,061 discloses their use in paints.

Despite the excellent biocidal (particularly fungicidal) activity attributable to pyrithlone salts, these compounds do have drawbacks for certain applications, most notably limited solubility in certain organic solvents and aqueous media. Accordingly, new compounds exhibiting excellent biocidal activity, but also exhibiting good solubility in organic solvents would be useful to the biocides manufacturing community.

One compound that exhibits good biocidal efficacy and solubility in shampoo formulations is 1-hydroxy-4-methyl-6-(2,4,4-trimethylpentyl)-2-Pyridone. Unfortunately, this compound is more expensive to manufacture than otherwise might be desired. This compound and related compounds are disclosed in U.S. Pat. No. 3,883,545; their use in combating dandruff is described in U.S. Pat. No. 4,185,106; and their use in an antidandruff shampoo is described in U.S. Pat. No. 4,711,775. U.S. Pat. No. 4,916,228 discloses the preparation of a broad class of 1-hydroxy-2-pyridones by a process comprising reacting a pyrone having a specified structural formula with a hydroxylammonium salt in the presence of at least one alkali metal carbonate and/or hydrogen carbonate.

A technical journal publication entitled "Quantitative Structure-Activity Analysis in a Series of Antimycotically Active N-Hydroxypyridones", Journal of Medicinal Chemistry, 1974, Vol. 17, No. 7, p. 753, describes a variety of 1-hydroxy-substituted-2-pyridones, including those having para-substitutions of —SCH$_2$C$_6$H$_4$Cl (compound 15 in Table II thereof) and —OCH$_2$C$_6$H$_4$Cl (compound 16 in Table II thereof), as having antimycotic activity. However, the method of preparation of these compounds is not described in this technical publication, and it is believed that these compounds were made from 6-chloro-2-pyrone which is not commercially available.

Other new biocides providing desired solubility characteristics, as well as new processes for their preparation, would be highly desired by the biocides manufacturing community.

SUMMARY OF THE INVENTION

In one aspect, the present invention relates to a compound of the formula:

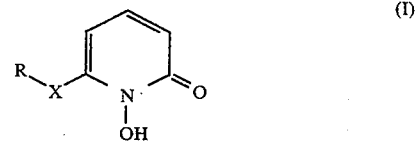

wherein X is an oxygen or sulfur moiety and R is substituted or unsubstituted hydrocarbon radical having between 1 and 20 carbon atoms, with the proviso that R is other than chlorobenzyl. Preferred hydrocarbon radicals are aliphatic hydrocarbons having between 3 and 15 carbons, more preferably a straight chain hydrocarbon having between 5 and 10 carbons. The term "substituted hydrocarbon" is intended to include substituents such as halogen such as chloro, iodo fluoro or bromo, alkoxy such as methoxy, ethoxy, propoxy or butoxy, nitro, thio, combinations thereof, and the like. Illustrative hydrocarbon groups include n-octyl, 2,4,4-trimethylpentyl, 3,5,5-trimethylhexyl, combinations thereof, and the like.

In another aspect, the present invention relates to a process for producing compound of Formula (I) wherein X is oxygen which comprises the steps of:

(a) reacting 2,6-dichloropyridine N-oxide, a hydroxy compound containing between 1 and 20 carbon atoms (such as an alcohol such as n-octanol or a phenol compound such as 4-methylphenol, preferably selected from the group consisting of alkyl, arylalkyl and aryl compounds containing at least one hydroxyl group, and combinations thereof) and a base (such as sodium hydroxide or potassium hydroxide), optionally in the presence of water or an organic solvent, at an elevated temperature to produce a corresponding 2-chloro-6-substituted-pyridine N-oxide and (b) reacting said with additional base to produce the corresponding 1-hydroxy-6-substituted pyridone.

The above process can be carried out sequentially or simultaneously in a single step. Surfactants and/or phase transfer catalysts are optionally employed to facilitate the step (a) reaction.

In still another aspect, this invention relates to a process for producing the compound of Formula (I), wherein X is sulfur, which comprises the following steps:

(a) reacting a 2,6-dichloropyridine N-oxide, a thiol compound having between 1 and 20 carbon atoms, (for example alkyl, arylalkyl and aryl compounds, and combinations thereof) and base (such as sodium hydroxide or potassium hydroxide) in an organic solvent at an elevated temperature to produce a corresponding 2-chloro-6-substituted-pyridine N-oxide and (b) reacting said 2-chloro-6-substituted-pyridine N-oxide with a base to produce the corresponding 1-hydroxy-6-substituted-2-pyridone.

The above process can be carried out sequentially or simultaneously in a single step. Surfactants and/or phase transfer catalysts are optionally employed to facilitate the step (a) reaction.

In yet another aspect, the present invention relates to an antimicrobial composition comprising a functional component selected from the group consisting of paint. adhesives, coatings, elastomers, sealants, shampoos, skin care medicaments and metalworking fluid plus an antimicrobially effective amount of a compound represented by the above Formula (I) or a salt of the compound of Formula (I). Illustrative salts include the amine salts, alkali metal and alkaline earth metal salts and the like.

In still another aspect, the invention relates to a method for inhibiting the growth of microorganisms by contacting said microorganisms with a composition containing an antimicrobial effective amount of a one of the above-described 1-hydroxy-6-substituted-2-pyridone compound or its salt of this invention and at least one component selected from the group consisting of soaps, shampoos, skin care medicaments, cosmetics, and other polymer compounds such as adhesives, coatings, elastomers, sealants and paints.

These and other aspects will become apparent upon reading the following detailed description of the invention.

DETAILED DESCRIPTION OF THE INVENTION

It has now been surprisingly discovered that a straightforward process can be employed to produce 1-hydroxy-6-substituted-2-pyridones, utilizing readily available starting materials. These compounds provide excellent antimicrobial efficacy and are inexpensive to produce.

The novel 1-hydroxy-6-substituted-2-pyridone compounds of this invention are represented by the following empirical structural formula:

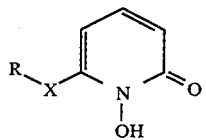

wherein X is an oxygen or sulfur moiety and R is substituted or unsubstituted hydrocarbon radical having between 1 and 20 carbon atoms, with the proviso that R is other than chlorobenzyl.

The reactions of the process of this invention are suitably conducted at atmospheric pressure, although higher or lower pressures may be used if desired. Suitable reaction temperatures for steps (a) and (b) range between a temperature of about 30° C. to about 150° C., preferably employing a reflux temperature of between about 70° C. and about 90° C. Total reaction time for the process of this invention can vary over a wide range, but is advantageously between 30 minutes and 5 hours for step (a) and between thirty minutes and 5 hours for step (b).

The reactions of the process of this invention are suitably carried out in the presence of a base and an organic solvent. Suitable bases include alkali metal hydroxides such as sodium hydroxide or potassium hydroxide, alkaline earth metal hydroxides such as calcium or magnesium hydroxide, pyridine, triethylamine and other tertiary amine bases, potassium carbonate, "DABCO" amine catalyst (1,4-diazabicyclo(2.2.2)octane), "DBU" (1,8-diazabicyclo(5.4.0)undec-7-ene), "DBN" (1,5-diazabicyclo(4.3.0)non-5-ene, t-butyltetramethyl-guanidine, combinations thereof, and the like. Preferred bases for step (a) are anhydrous, granular or powdered sodium or potassium hydroxide, and preferred bases for step (b) are concentrated aqueous solutions of sodium or potassium hydroxide having a concentration of base of between about 10% and about 90% by weight based upon the weight of the solution. Preferably, the base is employed in at least an amount equal to the number of moles for each reactant, and a molar excess of base relative to each reactant can be employed as desired.

The reactions of the process of this invention are suitably carried out in the presence of a solvent. Suitable organic solvents include, for example, ether, and acetone, methylene chloride, benzene, toluene, pyridine, tetrahydrofuran ("THF"), acetonitrile, dimethylsulfoxide ("DMSO"), dimethylformamide ("DMF"), and combinations thereof. Although the preferred solvent is acetonitrile, it is more preferred to run the reactions neat. As another alternative, a reactive solvent can be employed, if desired, for example by using an organic alcohol, e.g. isopropanol, or n-octanol, in an amount sufficient to provide the desired reactant and solvent characteristics.

The molar ratio of reactants for the process of this invention can vary over a wide range, but is preferably between 10:1 and 1:10, more preferably between 2:1 and 1:2, most preferably about 1:1.

The antimicrobial compositions of this invention suitably comprise an antimicrobially effective amount of a compound as defined by the structural formula given herein above and combinations thereof and at least one component selected from the group consisting of soaps, shampoos, skin care medicaments, cosmetics and paints. The antimicrobial compound can be employed as is or in the form of a salt, such as an amine salt such as the monoethanolamine ("MEA") salt, and the use of the salt form is preferred. By the term "antimicrobial effective amount" is meant an amount sufficient to impart to the compositions resistance against microbial attack by fungi and/or bacteria. Preferably the antimicrobial compounds are employed in the composition in a total amount of between about 0.01 and about 10 weight percent, more preferably between about 0.01 and about 5 weight percent, based upon the total weight of the composition. A particularly preferred use for the biocidal compounds of the present invention is in personal care products such as in shampoos and other hair care products, as well as in paint, paint bases and polymer compositions such as adhesive coatings, sealants, elastomers, acids and the like.

With respect to paints improved organic solubility and biocidal efficacy associated with the compounds of the present invention are expected to provide advantages when used in a wide variety of paints, including indoor and outdoor household paints, industrial and commercial paints and in particular marine paints for use, for example, or ships hulls.

Typically, a paint composition will contain a resin, a pigment and various optional additives such as thickening agent(s), wetting agents and the like, as is well known in the art. The resin is preferably selected from the group consisting of vinyl, alkyl, epoxy, acrylic, polyurethane and polyester resins, and combinations thereof. The resin is preferably employed in an amount of between about 20% and about 80% based upon the weight of the paint or paint base.

In addition, the paint composition of the present invention contains optional additional additives which have a favorable influence on the viscosity, the wetting power and the dispersibility, as well as on the stability to freezing and electrolytes and on the foaming properties. If a marine paint is being fabricated, the paint preferably contains a co-biocide such as cuprous oxide or copper thiocyanate, a swelling agent to cause the paint to gradually "slough off" in its marine environment, thereby causing renewed biocidal efficacy of newly exposed biocide at the surface of the paint in contact with the water medium of the marine environment. Illustrative swelling agents are naturally-occurring or synthetic clays, such as kaolin, montomorillonite (bentonite, clay mica (muscovite), and chlorite (hectonite), and the like. In addition to clays, other swelling agents, including natural or synthetic polymers, such as that commercially available as POLYMERGEL, have been found to be useful in the compositions of the present invention to provide the desired "sloughing off" effect. Swelling agents can be used singly or in combination. The total amount of optional additives is preferably no greater than 20% by weight, more preferably between about 1% and about 5% by weight, based upon the total weight of the paint composition.

Illustrative thickening agents include cellulose derivatives, for example methyl, hydroxyethyl, hydroxypropyl and carboxymethyl cellulose, poly(vinyl alcohol), poly (vinylpyrolidone), poly(ethylene-glycol), salts of poly(acrylic acid) and salts of acrylic acid/acrylamide copolymers.

Suitable wetting and dispersing agents include sodium polyphosphate, salts of low-molecular-weight poly(acrylic acid), salts of poly(ethane-sulfonic acid), salts of poly (vinyl-phosphonic acid), salts of poly(-maleic acid) and salts of copolymers of maleic acid with ethylene, 1-olefins with 3 to 18 carbon atoms and/or styrene.

In order to increase the stability to freezing and electrolytes there may be added to the paint composition various monomer 1,2-diols, for example glycol, propylene-glycol-(1,2), and butylene-glycol-(1,2) or polymers thereof, or ethoxylated compounds, for example reaction products of ethylene oxide with long-chain alkanols, amines, carboxylic acids, carboxylic acid amides, alkyd phenols, poly(propylene-glycol) or poly(butylene-glycol). The minimum temperature of film formation (white point) of the paint composition may be reduced by adding solvents, such as ethylene-glycol, butyl-glycol, ethyl-glycol acetate, ethyl-diglycol acetate, butyl-diglycol acetate, benzene or alkylated aromatic hydrocarbons. As defoaming agents there are suitable for example poly(propylene-glycol) and polysiloxanes.

The compounds of the present invention have many desirable attributes. They possess good antimicrobial activity and are compatible with components of conventional soaps, shampoos, skin-care medicaments, plastics and other polymer compositions and the like. These polymers are also non-volatile, hydrolytically-stable, thermally-stable and may be soluble in water and organic solvents. Furthermore, they form no undesirable colors in typical personal care items. Still further, they are expected to be favorably cost competitive with known antimicrobial additives used in conventional skin care formulations.

The following examples are intended to illustrate, but in no way limit the scope of, the present invention. In the examples, the term "g" denotes grams, "mol" denotes moles, and all percents are given on a weight basis unless otherwise specified.

EXAMPLES

Example 1

Preparation of 1-Hydroxy-6-isopropyloxypyridine-2(1H)-ones

The 0.82 g (0.0050 moles) of 2,6-dichlopyridine N-oxide and 0.78 g (0.013 moles) of isopropanol was reacted with 0.210 g (0.0050 moles) of ground sodium hydroxide in 8.2 ml of DMSO at 80° C. overnight to give 2-chloro-6-isopropyloxypyridine N-oxide. The excess of isopropanol was removed in vacuo and 0.800 g (0.020 mole) of ground sodium hydroxide was reacted at 3 hours at 100° C. to give 1-hydroxy-6-isopropyloxypyridine-2(1H)-one. After cooling, it was added 74 ml of water and was adjusted with 6N HCl to pH 5. It was extracted with ethyl acetate (3×25 ml). The ethyl acetate extract was washed with water (2×10 ml) and dried over sodium sulfate. The solution was saturated with sodium chloride and was extracted with ethyl acetate (3×25 ml). The ethyl acetate extract was washed with water (2×10 ml) and dried over sodium sulfate. The combined ethyl acetate extracts were filtered and stripped in vacuo to give 0.50 g (59%). It was recrystallized from 5 ml of ethyl acetate, 5 ml of hexanes, and activated carbon: mp 119°–120° C.

Example 2

Preparation of 1-Hydroxy-6-(2,4,4-trimethylpentyloxy)-pyridine-2-(1H)-one

The 0.82 g (0.0050 moles) of 2,6-dichloropyridine N-oxide and 0.664 g (98%) (0.0050 moles) of 2,4,4-trimethyl-1-pentanol was reacted with 0.211 g (0.0050 moles) of ground sodium hydroxide in 8.2 ml of DMSO at 100° C. overnight to give 2-chloro-6-(2,4,4-trimethypentyloxy) pyridine N-oxide. It was reacted with 0.600 g (0.015 moles) of ground sodium hydroxide at 100° C. for 4.5 hours to give 1-hydroxy-6-(2,4,4-trimethylpentyloxy)pyridine-2(1H)-one. After cooling, it was added 74 ml of water and was adjusted with 6N HCl to pH 3. It was extracted with ethyl acetate (3×25 ml). The combined ethyl acetate extract was washed with a saturated sodium chloride solution (2×10 ml) and dried over sodium sulfate. The ethyl acetate extract was filtered and stripped in vacuo to give 1.08 g (90%). It was recrystallized from ethyl acetate and hexanes: mp 133.5°–134° C.

Example 3

Preparation of 1-Hydroxy-6-(3,5,5-trimethylhexyloxy)-pyridine-2 (1H) -one

The 0.82 g (0.0050 moles) of 2,6-dichloropyridine N-oxide and 0.80 g (90%) (0.0050 moles) of 3,5,5-trimethyl-1-hexanol was reacted with 0.206 g (0.0050 moles) of ground sodium hydroxide in 8.2 ml of DMSO at 80° C. for 8.5 hours to give 2-chloro-6-(3,5,5trimethylhexyloxy)pyridine N-oxide. It was reacted with 0.600 g (0.015 moles) of ground sodium hydroxide at 80° C. for 4 hours to give 1-hydroxy-6-(3,5,5-trimethyl-hexyloxy) pyridine-2(1H)-one. After cooling, it was added 74 ml of water and was adjusted with 6N HCL to pH 3. The precipitate was filtered and washed with water to give 0.577 g (45%). It was recrystallized from ethyl acetate and hexanes: mp 130.5°–131° C.

Example 4

Preparation of 1-Hydroxy-6-octyloxypyridine-2-(1H)-one

The 0.82 g (0.0050 moles) of 2,6-dichloropyridine N-oxide and 0.658 g (99%) (0.0050 moles) of 1-octanol was reacted with 0.200 g (0.0050 moles) of ground sodium. hydroxide in 8.2 ml of DMSO at 80° C. for 4.5 hours to give 2-chloro-6-octyloxypyridine N-oxide. It was reacted with 0.600 g (0.015 moles) of ground sodium hydroxide at 80° C. for 2.5 hours to give 1-hydroxy-6-octyoxypyridine-2(1H)-one. After cooling, it was added 74 ml of water and was adjusted with 6N HCL to pH 3. The precipitate was filtered and washed with water to give 0.577 g (48%). It was recrystallized from ethanol and hexanes: mp 119°–120° C.

Example 5

Preparation of 1-Hydroxy-6-octylthiopyridine-2-(1H)-one

The 2.01 g (0.0122 moles) of 2,6-dichloropyridine N-oxide and 2.10 g (85%) (0.0122 moles) of 1-octylmercaptan was reacted with 0.488 g (0.0122 moles) of ground sodium hydroxide in 8.2 ml of DMSO at 80° C. for 6 hours to give 2-chloro-6-octylthiopyridine N-oxide. It was reacted with 1.47 g (0.0367 moles) of ground sodium hydroxide at 80° C. for 3 hours to give 1-hydroxy-6-octylthiopyridine-2(1H)-one. After cooling, it was added 180 ml of water and was adjusted with 6N HCL to pH 3. The precipitate was filtered, washed with water and washed with 150 ml of petroleum ether to give 1.34 g (43%).

Example 6

Preparation of 1-Hydroxy-6-octylsulfonylpyridine-2-(1H)-one

The 0.204 g (0.00080 moles) of 1-hydroxy-6-octylthiopyridine-2(1H)-one was reacted with 0.36 ml (0.0032). moles) of 30% hydrogen peroxide in 2.0 ml of glacial acetic acid for overnight at room temperature to give 1-hydroxy-6-octylsulfonylpyridine-2(1H)-one. It was stripped in vacuo and was then dissolved with ethanol and stripped in vacuo three times to give 0.22 g. It was recrystallized from acetone and petroleum ether.

Example 7

Preparation of 1-Hydroxy-6-thiophenylpyridine-2-(1H)-one

The 1.64 g (0.010 moles) of 2,6-dichloropyridine N-oxide and 1.11 g (99%) (0.010 moles) of thiophenol was reacted with 0.400 g (0.010 moles) of ground sodium hydroxide of 16.4 ml of DMSO at 80° C. for 5 hours to give 2-chloro-6-thiophenylpyridine N-oxide. It was reacted with 1.20 g (0.030 moles) of ground sodium hydroxide at 80° C. for 2.5 hours to give 1-hydroxy-6-thiophenylpyridine-2-(1H)-one. After cooling, it was added 148 ml of water and was adjusted with 6N HCl to pH 3. The precipitate was filtered, washed with water and washed with hexanes to give 1.64 g (75%). It was recrystallized from ethanol: mp 180°–181° C.

Example 8

Preparation of 1-Hydroxy-6-thiophenylsulfonypyridine-2-(1H)-one

The 1.00 g (0.00456 moles) of 1-hydroxy-6-thiophenylpyridine-2(1H)-one reacted with 1.30 ml (0.0114 moles) of 30% hydrogen peroxide in 5 ml of glacial acetic acid at room temperature overnight. The precipitate was dissolved with more 5 ml of glacial acetic acid and was then added 1.30 ml (0.0114 moles) of 30% hydrogen peroxide at room temperature over the weekend. The precipitate was filtered and washed with hexanes to give 0.624 g. The acetic acid and the hexanes were stripped in vacuo to give 0.45 g. The combined product gave 1.14 g (93%).

Example 9

Preparation of 1-Hydroxy-6-phenyloxypyridine-2-(1H)-one

The 0.82 g (0.0050 moles) of 2,6-dichloropyridine N-oxide and 0.47 g (0.0050 moles of phenol was reacted with 0.200 g (0.0050 moles) of ground sodium hydroxide in 8.2 ml of DMSO at 80° C. for 6 hours to give 2-chloro-6-phenyloxypyridine N-oxide. It was reacted with 0.600 g (0.015 moles) of ground sodium hydroxide at 80° C. for 3.5 hours to give 1-hydroxy-6-phenyoxypyridine-2-(1H)-one. After cooling, it was added 74 ml of water and was adjusted with 6N HCl to pH 3. The water solution was extracted with dichloromethane (2×25 ml) and was dried over sodium sulfate. The dichloromethane solution was stripped in vacuo to give 1.29 g which was purified with Flash Chromatography (9:1 ethyl acetate:methanol):0.82 (65%).

Determination of the Minimum Inhibitory Concentrations (MIC's) for Antimicrobial Compounds of this Invention Solutions of the experimental compounds in dimethyl sulfoxide were serially diluted in nutrient broth (Tryptic Soy Broth for bacteria and Sabouraud Dextrose Broth for fungi) in microtiter plates. Equal volumes of a broth suspension of bacteria ($10^6$ CFU/ml) or fungi ($10^5$ cells or spores/ml) were added to each dilution, and the plates were incubated at 37° C. (bacteria and yeast) or 28° C. (molds). Bacteria, yeast and molds were incubated two, five and seven days respectively before determining the highest inhibitory dilution.

TABLE I

| | MIC (ppm) MIC of the 1-hydroxy-6-substituted-2-pyridones | | | | | |
|---|---|---|---|---|---|---|
| Compound | A | B | C | D | E | F |
| Example 1 | 256 | ≧1024 | 128 | 512 | 512 | 512 |
| Example 2 | 64 | 64 | 8 | 32 | 8 | 16 |
| Example 3 | 32 | 32 | 2 | 2 | 16 | 2 |
| Example 4 | 32 | 16 | 4 | 2 | 32 | 4 |
| Example 5 | 256 | 16 | 8 | 32 | 8 | nt |
| Example 6 | 512 | 64 | 128 | 256 | 256 | nt |
| Example 7 | 64 | 128 | 16 | 64 | 64 | nt |
| Example 8 | 256 | 8 | 1024 | 1024 | 1024 | nt |
| Example 9 | 256 | 512 | 32 | 256 | 512 | nt |
| OCTOPIROX ® | 128 | 64 | 2 | 2 | 2 | 16–32 |

TABLE I-continued

| | MIC (ppm) MIC of the 1-hydroxy-6-substituted-2-pyridones | | | | | |
|---|---|---|---|---|---|---|
| Compound | A | B | C | D | E | F |
| biocide | | | | | | |

A = *Escherichia coli*
B = *Staphylococcus aureus*
C = *Candida albicans*
D = *Fusarium sp.*
E = *Aspergillus niger*
F = *Aureobasidium pullulans*
"nt" denotes not tested The results provided in Table 1 show that the compounds of the present invention provide MIC's that are sometimes better than those provided by a commercial biocide, OCTOPIROX® biocide, a product of Hoechst Company. Note that the compounds of Examples 3 & 4 provide particularly excellent MIC results.

What is claimed is:

1. A compound of the formula:

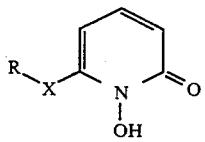

wherein X is an oxygen or sulfur moiety and R is substituted or unsubstituted hydrocarbon radical having between 1 and 20 carbon atoms, with the proviso that R is other than chlorobenzyl.

2. The compound of claim 1 wherein R is an aliphatic hydrocarbon having between 3 and 15 carbons.

3. The compound of claim 1 wherein R is a straight chain hydrocarbon having between 5 and 10 carbons.

4. The compound of claim 1 wherein R is an n-octyl moiety.

5. A process for producing the compound of the formula:

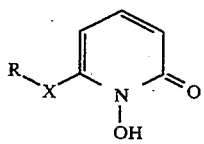

wherein X is an oxygen moiety and R is a substituted or unsubstituted hydrocarbon radical having between 1 and 20 carbon atoms, with the proviso that R is other than chlorobenzyl, which comprises the steps of:

(a) reacting a 2,6-dichloropyridine N-oxide, a hydroxy compound containing between 1 and 20 carbon atoms, and a base, in an organic solvent selected from the group consisting of ether, acetone, methylene chloride, benzene, toluene, pyridine, tetrahydrofuran, acetonitrile, dimethylsulfoxide, dimethylformamide, and combinations thereof, at an elevated temperature of between about 30° C. and about 150° C. to produce a corresponding 2-chloro-6-substituted-pyridine N-oxide, and (b) reacting said 2-chloro-6-substituted-pyridine N-oxide with additional base to produce a 1-hydroxy-6-substituted-2-pyridone compound.

6. The process of claim 5 wherein said solvent is selected from the group consisting of acetonitrile, dimethylsulfoxide, dimethylformamide, and combinations thereof.

7. The process of claim 5 wherein said hydroxy compound is employed in an amount sufficient to provide efficacy both as said solvent and as a reactant.

8. The process of claim 5 wherein said base of step (a) is sodium hydroxide or potassium hydroxide.

9. The process of claim 5 wherein said base of step (b) is sodium hydroxide or potassium hydroxide.

10. A process for producing the compound of the formula:

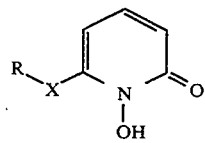

wherein X is a sulfur moiety and R is a substituted or unsubstituted hydrocarbon radical having between 1 and 20 carbon atoms, with the proviso that R is other than chlorobenzyl, which comprises the steps of:

(a) reacting a 2,6-dichloropyridine N-oxide, a thiol compound having between 1 and 20 carbon atoms, and a base, in an organic solvent selected from the group consisting of ether, acetone, methylene chloride, benzene, toluene, pyridine, tetrahydrofuran, acetonitrile, dimethylsulfoxide, dimethylformamide, and combinations thereof, at an elevated temperature of between about 30° C. and about 150° C. to produce a corresponding 2-chloro-6-substituted-oxypyridine N-oxide, and (b) reacting said 2-chloro,6-substituted oxypyridine N-oxide with additional base to produce the corresponding 1-hydroxy-6-substituted-2-pyridone.

11. A process for producing a compound of the formula:

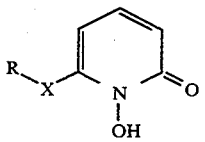

wherein X is a sulfur moiety and R is a substituted or unsubstituted hydrocarbon radical having between 1 and 20 carbon atoms, with the proviso that R is other than chlorobenzyl, which comprises the steps of:

(a) reacting a 2,6-dichloropyridine N-oxide, a thiol compound having between 1 and 20 carbon atoms, and a base, in an organic solvent selected from the group consisting of acetonitrile, dimethylsulfoxide, dimethylformamide, and combinations thereof, at an elevated temperature of between about 30° C.

and about 150° C. to produce a corresponding 2-chloro-6-substituted-oxypyridine N-oxide, and (b) reacting said 2-chloro,6-substituted oxypyridine N-oxide with additional base to produce the corresponding 1-hydroxy-6-substituted-pyridone.

12. The process of claim 10 wherein said thiol compound is employed in an amount sufficient to provide efficacy both as a solvent and as a reactant.

13. The process of claim 10 wherein said base of step (a) is sodium hydroxide or potassium hydroxide.

14. The process of claim 10 wherein said base of step (b) is sodium hydroxide or potassium hydroxide.

15. The process of claim 5 wherein steps (a) and (b) are conducted simultaneously in a single step.

16. The process of claim 10 wherein steps (a) and (b) are conducted simultaneously in a single step.

17. The compound of claim 1 wherein X is oxygen and R is an octyl or trimethylhexyl moiety.

18. The compound according to claim 1 wherein X in said formula is oxygen and R is an octyl or trimethylhexyl moiety.

* * * * *